(12) United States Patent
Irvin et al.

(10) Patent No.: US 7,601,747 B1
(45) Date of Patent: *Oct. 13, 2009

(54) ONE-POT PROCESS FOR MAKING DI-FUNCTIONAL DI-TETRAZOLE DIOLS TO PRODUCE TETRAZOLE BASED POLYMERS

(75) Inventors: David J. Irvin, Ridgecrest, CA (US); Mark H. Mason, Inyokern, CA (US); Richard Hollins, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 450 days.

This patent is subject to a terminal disclaimer.

(21) Appl. No.: 11/151,185

(22) Filed: May 27, 2005

(51) Int. Cl.
*A61K 31/41* (2006.01)
(52) U.S. Cl. ...................... 514/381; 514/382
(58) Field of Classification Search ............. 548/250, 548/251; 514/381, 382
See application file for complete search history.

(56) References Cited

U.S. PATENT DOCUMENTS 5,053,086 A * 10/1991 Henry et al. ............... 149/19.4

OTHER PUBLICATIONS

Finnegan, et al., JACS, (1958), vol. 80, pp. 3908-3911, especially pp. 3909-3911.*
Copending U.S. Appl. Nos. 11/151,178 and 11/151,180.*
Demko, et al. J. Org. Chem. 2001, 66, pp. 7945-7950.*

* cited by examiner

*Primary Examiner*—Rebecca L Anderson
*Assistant Examiner*—Shawquia Young
(74) *Attorney, Agent, or Firm*—Brian F. Drazich; Charlene A. Haley

(57) ABSTRACT

A one-pot process for making energetic cast cured binders making di-tetrazoles to produce di-functional di-tetrazole diols for making tetrazole base polymers. Embodiments of the present invention relate generally to a process for preparation of a di-functional monomer including reacting an effective amount of nitrile(s) with inorganic azide and a divalent zinc salt in a first solvent, cooling to room temperature producing a di-tetrazole, purifying said di-tetrazole by recrystallization in a second solvent, and reacting an effective amount of said purified di-tetrazole with a third solvent, a soluble reversible or non-reversible base, and 2-chloro-ethanol, cooling to room temperature producing a di-tetrazole diol and is prepared in a one-pot process. Embodiments of the present invention further include the monomers produced by the one-pot process described herein.

14 Claims, No Drawings

ONE-POT PROCESS FOR MAKING DI-FUNCTIONAL DI-TETRAZOLE DIOLS TO PRODUCE TETRAZOLE BASED POLYMERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

There is a need for novel energetic binders to increase the performance of pyrotechnics, gun propellants, rocket propellants, air-bag gas generator propellants, and explosives. Depending on the application, these materials are typically 3-25% binder by mass. Therefore, improvements to the energy content, mechanical properties, or insensitive munitions properties of the polymeric binder can have significant affects on the performance of the energetic material in question.

In general many pyrotechnics, propellants, explosives are comprised of a polymeric binder that holds one or more energetic solids in a plastic matrix. The polymeric binder serves many roles in these materials. Initially the polymer can aid in processing. In fact, the properties of the polymer will significantly affect how a material is processed, whether it is cast or pressed or extruded. Furthermore, the polymer mechanically holds all the ingredients together, serving as a structural element literally binding together the final material. This role is especially critical in rocket propellants, because cracks and voids in the propellant will lead to motor grain failure, often with catastrophic results. The binder serves many safety functions. The binder physically coats the energetic solids in these materials, this provides a physical buffer to minimize the physical and chemical interaction of reactive solids with each other. This generally lowers the electrostatic discharge, impact, and friction sensitivity of the final material. In some materials, especially rocket propellants, the binder also serves as a fuel when the hydrocarbon polymer is combusted by the oxidizer. However, the binder generally diminishes the performance (detonation pressure and velocity) of most explosives. To improve the performance of explosives with significant binder content, and to increase the energy density of propellants energetic polymers are needed.

While there are energetic binders available (polyglycidyl nitrate (PGN), polyglycidyl azide (GAP), azidomethyl-methyl-oxetane (AMMO), bis((azido-methyl)oxetane) (BAMMO), nitratomethyl-methyloxetane (NMMO), etc.) the safety benefits of increasing binder content are lost because these materials contain either organic azides or nitrate esters (or both). These functional groups are chemically unstable, easily ignited, and generally create reactive fragments on aging. In fact, propellants that utilize nitrate esters generally require expensive monitoring programs throughout their life cycle to insure both adequate safety properties and performance as the propellant ages. The cost of such monitoring is often cited as one reason most modern explosives do not to use nitrate esters as binder materials. Furthermore, the energetic groups are pendant moieties attached to the polymer, but not incorporated into the polymer backbone. This impairs the physical properties of these polymers and causes the formulator to need a higher weight percent of binder in order to achieve adequate coating. In short, there is a need for improved energetic binders to address safety, performance, aging, and processing requirements.

While tetrazoles are somewhat less energetic than azides or nitrates, the bis-alkyltetrazoles of interest are more thermally stable and substantially less chemically reactive. Higher percentages of these binders could be used without anticipating negative safety consequences. Furthermore, the energetic functionality is built into the polymer backbone, minimizing the total moles of pendant atoms. This is anticipated to yield a binder with superior physical properties. A dihydroxy-terminated bis-tetrazole (2,2 Bis((2-ethanol)-1 or 2H-tetrazole)-propane or BETP) has been synthesized on the multigram scale. Initial differential scanning calorimetery (DSC) analysis shows this pre-polymer has promise as an energetic cured urethane binder for explosives and propellants and gas generatos.

U.S. Pat. No. 5,053,086 issued on Oct. 1, 1991 to Henry, et al., which teaches gas generating compositions containing energetic high nitrogen such as ammonium 5-nitraminotetrazole and 5,5'-bitetrazole. This work yielded polymeric binders that are too rigid and "glassy" for the intended application. The chemical structure of the present invention polymers builds more flexibility into the backbone, yielding improved elastomers. Further research by Demko teaches the addition of sodium azide to nitrites to give 1H-tetrazoles in water with zinc salts as catalysts. (Demko, Z. P.; Sharpless, K. B. "Preparation of 5-substituted 1H-tetrazoles from nitrites in water." *J. Org. Chem.* 2001, 66, 7945). This step is only one method to obtain the tetrazole intermediate. Further reaction is necessary to produce the alcohol-based monomers. The addition of the alkyl alcohol is two fold: first, the short alkyl chain adds flexibility, solubility; second, the alcohol group allows for the production of stable polyurethanes. Polymerization of the tetrazole would produce the less stable polyurea.

Tetrazole compounds have application in many fields including, but not limited to, chemistry, ligands, metabolically stable surrogate for a carboxylic acid group, and material sciences including explosives and propellants and air bag gas generators.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments and in the appended claims.

DETAILED DESCRIPTION OF THE INVENTION

Embodiments of the present invention generally relate to a process for preparation of a di-functional monomer having the general structure (I) comprising: reacting an effective amount of

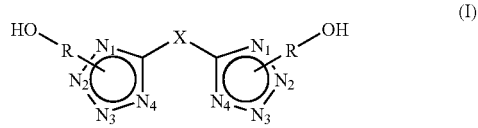

nitrile(s) with inorganic azide and a divalent zinc salt in a first solvent at a temperature in the range of about 70° C. to about 170° C. for a time period in the range of about 1 to 24 hours, wherein the nitrile(s) having the general structure (II), wherein [X] comprises at least one group of alkyls, aryls, and oligoethers; cooling to room temperature producing a di-tetrazole having the general structure

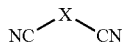
(II)

(III), wherein [H] is chemically bonded to $N_1$ or $N_2$ position of the di-tetrazole, wherein [X] comprises at least one group of alkyls, aryls, and oligoethers; purifying the di-tetrazole by

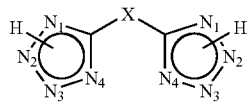
(III)

recrystallization in a second solvent; reacting an effective amount of the purified di-tetrazole with a third solvent, a soluble reversible or non-reversible base, and 2-chloro-ethanol at a temperature in the range of about 70° C. to about 150° C. for a time period in the range of about 1 to about 24 hours, cooling to room temperature producing a di-tetrazole diol having the general structure (I), wherein [X] comprises at least one group of alkyls, aryls, and oligoethers, wherein [R] comprises at least one group of alkyls, aryls, and oligoethers, wherein [R] is chemically bonded to $N_1$ or $N_2$ position of the di-tetrazole diol (I); and wherein the structure (I) is prepared in a one-pot process. Embodiments of the present invention further include the monomers produced by the process described herein.

The nitrile(s) utilized include, but not limited to, at least one of dimethyl-malononitrile and malononitrile. When dimethyl-malononitrile is utilized it includes 2,2-dimethyl-malononitrile. In embodiments, the inorganic azide includes at least one of sodium azide, lithium azide, and potassium azide. In the method for making tetrazole diols, the divalent salts utilized include zinc bromide. The first solvent is polar which includes at least one of water, alcohol including 2-propanol, dimethylformanide, dimethylacetamide, and N-methylpyrrolidinone. The second solvent includes at least one of ethyl acetate and hexane. The third solvent is polar which includes at least one of water, alcohol including 2-propanol, dimethylformanide, dimethylacetamide, and N-methyl pyrrolidinone. In embodiments of the present invention, a soluble base is utilized. The soluble reversible base includes at least one of sodium hydroxide, lithium hydroxide, and potassium hydroxide. The soluble non-reversible base includes at least one of sodium hydride, lithium hydride, and potassium hydride.

When each di-tetrazole is produced it includes its isomer and each di-tetrazole isomer is independent of other di-tetrazole isomers. In embodiments of the present invention, the tetrazole diol is alkylated tetrazole diol and each alkylated tetrazole diol includes its isomers and each alkylated tetrazole isomer is independent of other alkylated tetrazole isomers. In some embodiments, the alkylated tetrazole diol includes di-tetrazole diol. In other embodiments, the tetrazole diol is arylated tetrazole diol and each arylated tetrazole diol includes its isomers and each arylated tetrazole isomer is independent of other arylated tetrazole isomers. Yet still in other embodiments, the arylated tetrazole diol includes di-tetrazole diol or an oligoether tethered diol. In other methods the tetrazole diol produces di-tetrazole diol.

In embodiments of the present invention when the nitrile, 2,2-dimethyl-malononitrile is utilized, the di-tetrazole diol (I) produced is Bis(N-ethanol-5-tetrazolyl)propane. The Bis(N-ethanol-5-tetrazolyl)propane in this embodiment includes at least one of 2,2-Bis(5-(1-N-ethanol-5-tetrazolyl)propane (Ia), 2,2-Bis(5-(2-N-ethanol-5-tetrazolyl)propane (Ib), and 2-(5-(1-N-ethanol-5-tetrazolyl)-2-(5-(2-N-ethanol-5-tetrazolyl)propane (Ic).

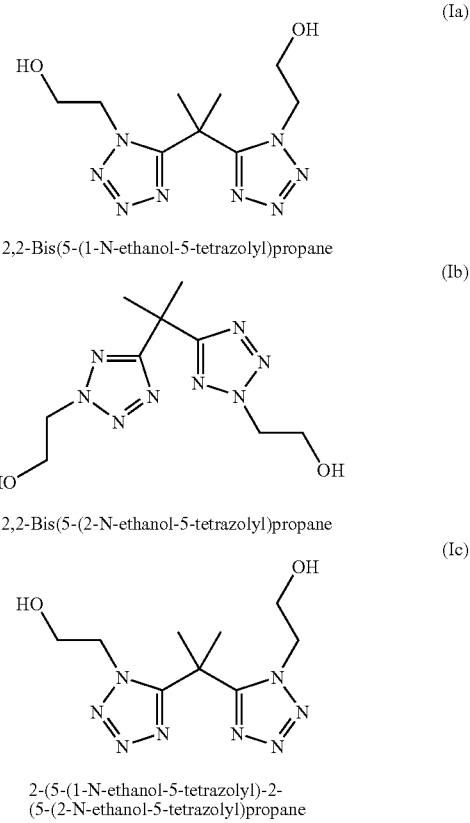

(Ia) 2,2-Bis(5-(1-N-ethanol-5-tetrazolyl)propane (Ib) 2,2-Bis(5-(2-N-ethanol-5-tetrazolyl)propane (Ic) 2-(5-(1-N-ethanol-5-tetrazolyl)-2-(5-(2-N-ethanol-5-tetrazolyl)propane Also, when embodiments of the present invention include the nitrile, 2,2-dimethyl-malononitrile is utilized, and the purified di-tetrazole (III) produced is Bis(5-tetrazolyl)propane. The Bis(5-tetrazolyl)propane in this embodiment includes at least one of 2,2-Bis(5-(1-[H]-tetrazolyl)propane (IIIa), 2,2-Bis(5-(2-[H]-tetrazolyl)propane (IIIb), and 2-(5-(1-[H]-tetrazolyl)-2-(5-(2-[H]-tetrazolyl)propane (IIIc).

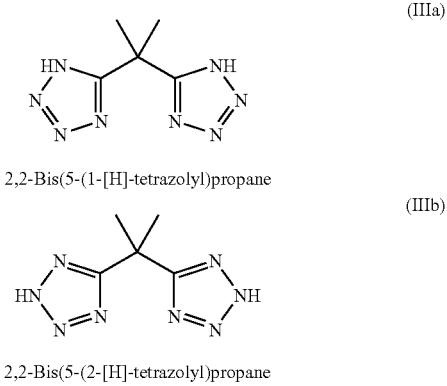

(IIIa) 2,2-Bis(5-(1-[H]-tetrazolyl)propane (IIIb) 2,2-Bis(5-(2-[H]-tetrazolyl)propane

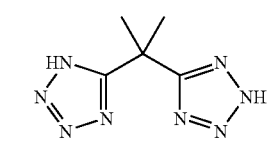

2-(5-(1-[H]-tetrazolyl)-2-
(5-(2-[H]-tetrazolyl)propane

In other embodiments of the present invention when the nitrile, malononitrile is utilized, the di-tetrazole diol (I) produced is Bis(N-ethanol-5-tetrazolyl)methane. The Bis(N-ethanol-5-tetrazolyl)methane in this embodiment includes at least one of 2,2-Bis(5-(1-N-ethanol-5-tetrazolyl)methane (Id), 2,2-Bis(5-(2-N-ethanol-5-tetrazolyl)methane (Ie), and 2-(5-(1-N-ethanol-5-tetrazolyl)-2-(5-(2-N-ethanol-5-tetrazolyl)methane (If).

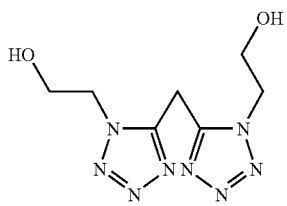

Bis(5-(1-N-ethanol-5-tetrazolyl) methane

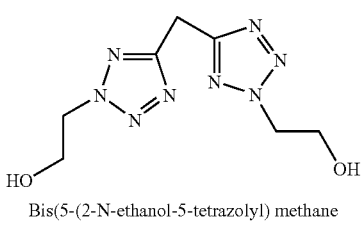

Bis(5-(2-N-ethanol-5-tetrazolyl) methane

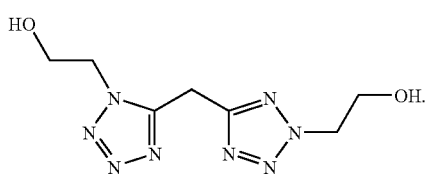

5-(1-N-ethanol-5-tetrazolyl-
5-(2-N-ethanol-5-tetrazolyl methane

When embodiments of the present invention include nitrile and malononitrile is utilized, the purified di-tetrazole (III) produced is Bis(5-tetrazolyl)methane. The Bis(5-tetrazolyl) methane in this embodiment includes at least one of 2,2-Bis (5-(1-[H]-tetrazolyl)methane (IIId), 2,2-Bis(5-(2-[H]-tetrazolyl)methane (IIIe), and 2-(5-(1-[H]-tetrazolyl)-2-(5-(2-[H]-tetrazolyl)methane (IIIf).

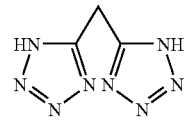

Bis(5-(1-[H]-tetrazolyl)methane

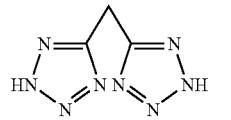

Bis(5-(2-[H]-tetrazolyl methane

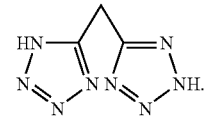

5-(1-[H]-tetrazolyl-
5-(2-[H]-tetrazolyl methane

EXPERIMENTAL RESULTS AND PROPHETIC EXAMPLES

The focus of the synthesis was on the new two monomers. Due to materials cost, the same chemistry on malonitrile was tested to produce the diol. For a higher nitrogen content and a lower equivalent weight, the tetra-alcohol was synthesized from 1,1,3,3 tetracyanopropane. The resulting monomers will be test polymerized using the current formulation catalyst, triphenyl bismuth and analyzed. We will deliver to the formulations group ~25 g of each of the two monomers for evaluation and testing.

The synthesis and subsequent polymerization of tetrazole-based polyols is a three-step process from which commercially available materials were utilized. Commercial nitrites are converted to the tetrazole using sodium azide and zinc bromide in water (occasionally, 2-pronanol is added if the nitrile is insoluble in water) giving good yields (60-95%). The resultant materials are purified by recrystallization (see Demko). In the second step, the novel idea of utilizing water, sodium hydroxide, and 2-chloro-ethanol in high yields (~75%) with the subsequent monomers being purified by column chromatography. At this point the equivalent weight of the alcohol is determined and the polymerization is optimized. A performance test on this transformation using dimethylmalonitrile to produce test di-tetrazole diol.

Example of One-Pot Synthesis

In a vial equipped with a stir bar, malononitrile (1 g), sodium azide (1.5 g), zinc bromide (5.5 g) and water (30 mL) were combined and heated to 100° C. After 2 hours, 2-chloroethanol (~5 mL) was added and the resulting solution was heated to 100° C. After 24 hours, the liquids were removed via reduced pressure evaporation to yield a tan, viscous oil. The mixture was dissolved with 1M HCl and then extracted with chloroform and ethyl acetate to yield the bis(ethanol-5-tetrazolyl)methane in fair yield. The remainder of the product was dissolved in the water layer.

While the invention has been described, disclosed, illustrated and shown in various terms of certain embodiments or modifications which it has presumed in practice, the scope of the invention is not intended to be, nor should it be deemed to

What is claimed is:

1. A process for preparation of a structure of Formula (I)

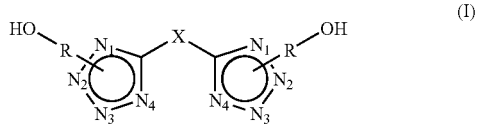

wherein "X" is a $C_1$ to $C_3$ alkyl group and "R" is an alkyl group chemically bonded to $N_1$ or $N_2$ position of the di-tetrazole diol of Formula (I); comprising:

reacting in a first solvent an inorganic azide and a divalent zinc salt with a nitrile of Formula (II),

where "n" of said nitrile is 2 to 9 and "X" is a $C_1$ to $C_3$ alkyl group, at a temperature in the range from about 70° C. to about 170° C. for a time period in the range from about 1 hour to about 24 hours, allowing contact of reactants, to form a di-tetrazole of Formula (III),

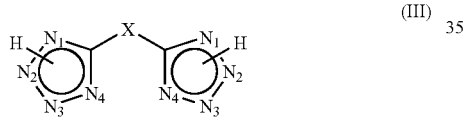

wherein "H" is chemically bonded to $N_1$ or $N_2$ position of said di-tetrazole, and "X" is a $C_1$ to $C_3$ alkyl group;

isolating said di-tetrazole by recrystallization from a suitable second solvent;

reacting said di-tetrazole in a third solvent with a soluble reversible or non-reversible base and 2-chloro-ethanol at a temperature in the range from about 70° C. to about 150° C. for a time period in the range from about 1 hour to about 24 hours, allowing contact of reactants, to form a reaction mixture containing a di-tetrazole diol of Formula (I); and, extracting said di-tetrazole diol of Formula (I) from the reaction mixture.

2. The process according to claim 1, wherein said nitrile(s) comprises at least one of dimethyl-malononitrile and malononitrile.

3. The process according to claim 2, wherein said dimethyl-malononitrile includes 2,2-dimethyl-malononitrile.

4. The process according to claim 1, wherein said inorganic azide includes at least one sodium azide, lithium azide, and potassium azide.

5. The process according to claim 1, wherein said divalent salt is zinc bromide.

6. The process according to claim 1, wherein said first solvent is polar which comprises at least one of water, alcohol including 2-propanol, dimethylformanide, dimethylacetamide, and N-methylpyrrolidinone.

7. The process according to claim 1, wherein said second solvent comprises at least one of ethyl acetate and hexane.

8. The process according to claim 1, wherein said third solvent is polar which comprises at least one of water, alcohol including 2-propanol, dimethylformanide, dimethylacetamide, and N-methylpyrrolidinone.

9. The process according to claim 1, wherein said soluble reversible base comprises at least one of sodium hydroxide, lithium hydroxide, and potassium hydroxide.

10. The process according to claim 1, wherein said soluble non-reversible base comprises at least one of sodium hydride, lithium hydride, and potassium hydride.

11. The process according to claim 1, wherein said di-tetrazole diol of Formula (I) is a bis-tetrazole diol.

12. The process according to claim 1, wherein said di-tetrazole diol (I) is Bis(N-ethanol-5-tetrazolyl)propane, said Bis(N-ethanol-5-tetrazolyl)propane comprises at least one of 2,2-Bis(5-(1-N-ethanol-5-tetrazolyl)propane (Ia), 2,2-Bis(5-(2-N-ethanol-5-tetrazolyl)propane (Ib), and 2-(5-(1-N-ethanol-5-tetrazolyl)-2-(5-(2-N-ethanol-5-tetrazolyl)propane (Ic);

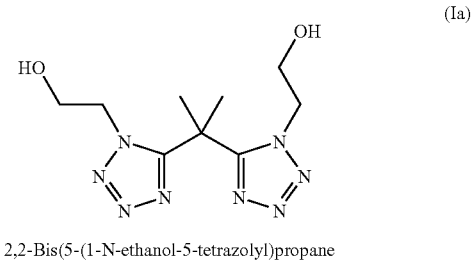

2,2-Bis(5-(1-N-ethanol-5-tetrazolyl)propane

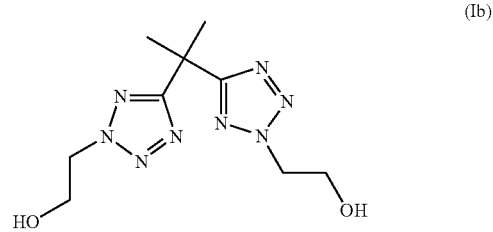

2,2-Bis(5-(2-N-ethanol-5-tetrazolyl)propane

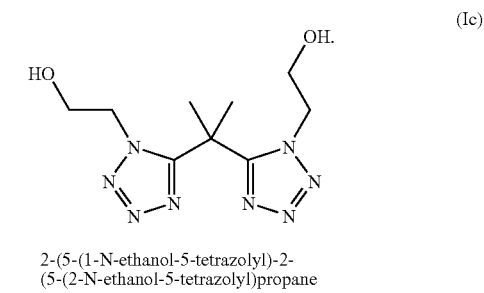

2-(5-(1-N-ethanol-5-tetrazolyl)-2-
(5-(2-N-ethanol-5-tetrazolyl)propane

13. The process according to claim 1, wherein said di-tetrazole diol (I) is Bis(N-ethanol-5-tetrazolyl)methane, said Bis(N-ethanol-5-tetrazolyl)methane comprises at least one of 2,2-Bis(5-(1-N-ethanol-5-tetrazolyl)methane (Id), 2,2-Bis (5-(2-N-ethanol-5-tetrazolyl)methane (Ie), and 2-(5-(1-N-ethanol-5-tetrazolyl)-2-(5-(2-N-ethanol-5-tetrazolyl)methane (If);

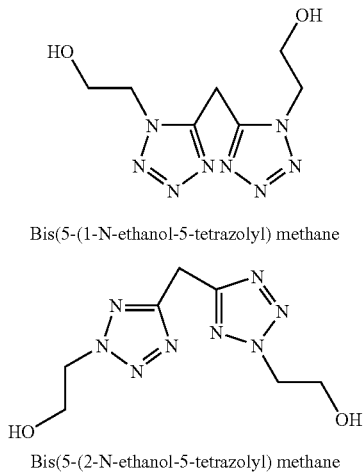
Bis(5-(1-N-ethanol-5-tetrazolyl) methane
(Id)
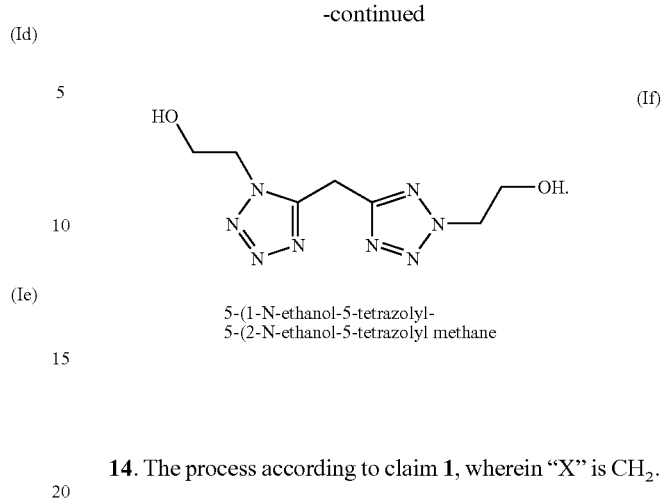
5-(1-N-ethanol-5-tetrazolyl-
5-(2-N-ethanol-5-tetrazolyl methane
(If)
Bis(5-(2-N-ethanol-5-tetrazolyl) methane
(Ie)
14. The process according to claim 1, wherein "X" is $CH_2$.
* * * * *